United States Patent
Laserson et al.

(10) Patent No.: US 11,797,647 B2
(45) Date of Patent: Oct. 24, 2023

(54) TWO STAGE DETECTOR FOR IDENTIFICATION OF A VISUAL FINDING IN A MEDICAL IMAGE

(71) Applicant: Nano-X AI Ltd., Shefayim (IL)

(72) Inventors: Jonathan Laserson, Tel Aviv (IL); Amit Oved, Rosh HaAyin (IL); Moti Kadosh, RaAnana (IL)

(73) Assignee: Nano-X AI Ltd., Shefayim (IL)

( * ) Notice: Subject to any disclaimer, the term of this patent is extended or adjusted under 35 U.S.C. 154(b) by 330 days.

(21) Appl. No.: 17/216,862

(22) Filed: Mar. 30, 2021

(65) Prior Publication Data

US 2022/0318565 A1  Oct. 6, 2022

(51) Int. Cl.
*G06F 18/214* (2023.01)
*G06T 7/00* (2017.01)
(Continued)

(52) U.S. Cl.
CPC ...... *G06F 18/2148* (2023.01); *G06F 18/2431* (2023.01); *G06N 20/00* (2019.01); *G06T 7/0012* (2013.01); *G16H 30/40* (2018.01); *A61B 6/502* (2013.01); *G06T 2207/20081* (2013.01); *G06T 2207/20084* (2013.01);
(Continued)

(58) Field of Classification Search
CPC ........ G16H 30/40; G16H 50/20; G16H 50/70; G16H 15/00; G16H 30/20; G16H 40/60; G16H 50/30; G16H 70/60; G16H 10/60; G16H 50/50; G16H 40/20; G16H 70/20; G16H 20/10; G16H 20/40; G16H 40/63; G16H 40/67; G06F 18/2431; G06F 18/214; G06F 17/18; G06F 18/23; G06F 18/24; G06F 18/2415; G06F 16/583;
(Continued)

(56) References Cited

U.S. PATENT DOCUMENTS

2019/0304092 A1* 10/2019 Akselrod-Ballin .... G06N 3/084
2019/0362855 A1* 11/2019 Ma ........................ G06T 7/0016
2022/0130033 A1*  4/2022 Rashidi ................. G06T 7/0008

OTHER PUBLICATIONS

Conant et al. "Improving Accuracy and Efficiency With Concurrent Use of Artificial Intelligence for Digital Breast Tomosynthesis", Radiology Artificial Intelligence, 1(4): e180096-1 - e180096-12, Jul. 31, 2019.
(Continued)

*Primary Examiner* — Ajibola A Akinyemi

(57) ABSTRACT

There is provided a method, comprising feeding a medical image into a detector component trained on a first training dataset of medical images annotated with ground truth boxes depicting a visual finding, obtaining boxes each associated with a respective box score indicative of likelihood of the visual finding, converting each respective box into a respective patch, feeding patches into a patch classifier trained on a second training dataset that includes patches extracted from the ground truth box labels of the first training dataset, wherein a patch score for a patch corresponds to a box score obtained from a box corresponding to the patch, obtaining patch scores indicative of likelihood of the visual finding being depicted, and computing a dot product of the box scores and the patch scores, and providing the dot product as an image-level indication of likelihood of the visual finding being depicted in the medical image.

20 Claims, 10 Drawing Sheets

(51) Int. Cl.
  *G16H 30/40* (2018.01)
  *G06N 20/00* (2019.01)
  *G06F 18/2431* (2023.01)
  *A61B 6/00* (2006.01)

(52) U.S. Cl.
  CPC .......... *G06T 2207/30068* (2013.01); *G06T 2207/30096* (2013.01); *G06V 2201/03* (2022.01)

(58) Field of Classification Search
  CPC .... G06F 18/217; G06F 18/2413; G06F 18/28; G06F 18/285; G06F 40/205
  USPC ........................................................ 382/128
  See application file for complete search history.

(56) References Cited

OTHER PUBLICATIONS

He et al. "Deep Residual Learning for Image Recognition", 2016 IEEE Conference on Computer Vision and Pattern Recognition, CVPR, L:as Vegas, Nv, USA. Jun. 27-30, 2016, p. 770-778, Jun. 27, 2016.

Lin et al. "Feature Pyramid Networks for Object Detection", 2017 IEEE Conference on Computer Vision and Pattern Recognition, CVPR, Honolulu. Hl, USA, Jul. 21-26, 2017, p. 936-944, Jul. 21, 2017.

Lin et al. "Focal Loss for Dense Object Detection", 2017 IEEE International Conference on Computer Vision. ICCV, Venice, Italy, Oct. 22-29, 2017, p. 2999-3007, Oct. 22, 2017.

Mckinney et al. "International Evaluation of An AI Systemfor Breast Cancer Screening", Nature, 577(7788):89-94, Published Online Jan. 1, 2020.

Rodriguez-Ruiz el al. "Detection of Breast Cancer Willi Mammography: Effect of an Artificial Intelligence Support System". Radiology, 290(2): 305-314, Published Online Nov. 20, 2018.

Szegedv et al. "Rethinking the Inception Architecture for Computer Vision", 2016 IEEE Conference on Computer Vision and Pattern Recognition, CVPR, Las Vegas, Nv, USA, Jun. 27-30, 2016, p. 2818-2826, Jun. 27, 2016.

\* cited by examiner

| Source | Country | no. of institutions | total cases |
|---|---|---|---|
| InterMountain Healthcare (IMH) | USA | 117 | 416846 |
| Clalit | Israel | 50 | 317315 |
| Optimam | UK | 3 | 9214 |

FIG. 7

| Category | Description | Clalit | Optimam | IMH |
|---|---|---|---|---|
| Validated Negative (VN) | Normal cases with at least 2 years of normal follow ups | 31,581 | 3,630 | 89,259 |
| Negative (N) | Normal cases with no recorded follow up or with a non-negative follow up within 2 years | 132,408 | 464 | 305,910 |
| Validated Positive (VP) | A biopsy was performed based on the scan and follow up inspections (e.g diagnostic scan, US, MRI), with positive outcome. | 2,275 | 3,159 | 1,248 |
| Positive (P) | BIRADS 5 cases without biopsy outcome information. | 958 | 0 | 618 |
| Validated Benign (VB) | A biopsy was performed based on the scan and follow up inspections (e.g diagnostic scan, US, MRI), with a negative outcome. | 2,299 | 245 | 2,881 |
| Benign (B) | BIRADS 3 cases followed by normal exams for at least 2 years | 1,390 | 0 | 2,748 |

FIG. 8

| Category | no. of studies | | |
|---|---|---|---|
| | Clalit | IMH | Optimam |
| Validated Negative | 24,440 | 22,372 | 67 |
| Negative | 10,853 | - | 321 |
| Validated Benign | 2,077 | 2,175 | 159 |
| Validated Positive | 1,956 | 763 | 1,809 |
| Benign | 1,096 | 1,852 | - |
| Positive | 883 | 456 | - |

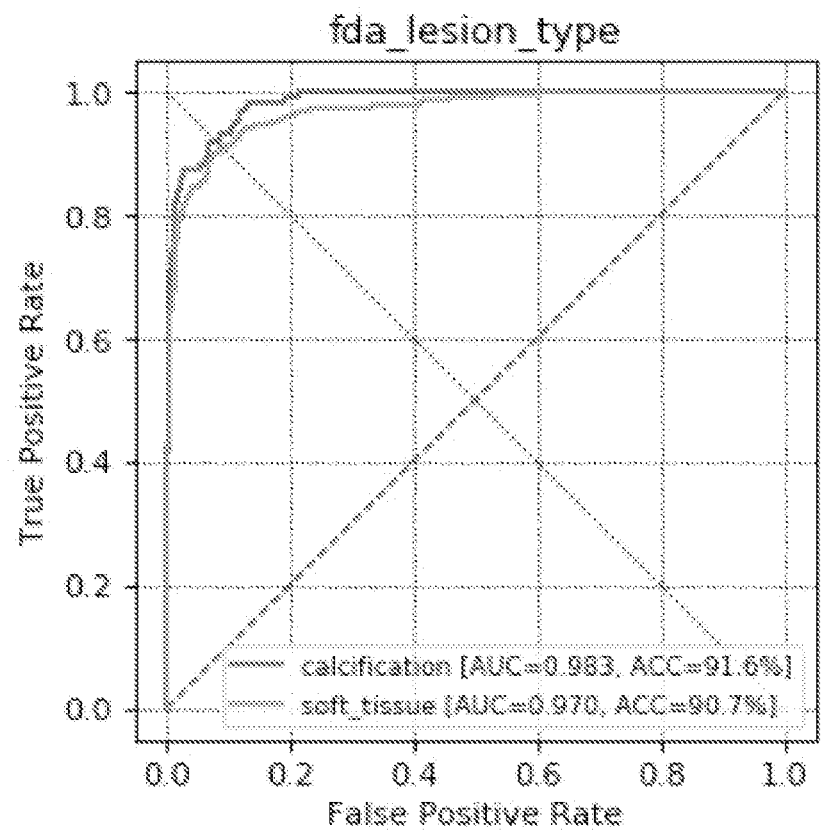
FIG. 10 - continued

TWO STAGE DETECTOR FOR IDENTIFICATION OF A VISUAL FINDING IN A MEDICAL IMAGE

FIELD AND BACKGROUND OF THE INVENTION

The present invention, in some embodiments thereof, relates to machine learning models and, more specifically, but not exclusively, to systems and method for training machine learning models to identify visual finding(s) in medical images, and inference by the trained machine learning models.

Machine learning models, such as classifiers and/or detections, implemented for example as neural networks, are being increasingly used in medical applications to help identify important visual findings in medical images, for example, cancer. Such machine learning models are trained on a training dataset of sample medical images labelled with an indication of whether the respective sample medical image depicts a visual finding or not.

SUMMARY OF THE INVENTION

According to a first aspect, a computer implemented method of identifying a visual finding in a medical image using a two-stage detector, comprises: feeding a medical image into a detector component implemented as a ML model trained on a first training dataset of a plurality of medical images annotated with ground truth boxes depicting a visual finding therein, obtaining as an outcome of the detector component, a plurality of boxes for the medical image, each respective box associated with a respective box score indicative of likelihood of the visual finding being depicted therein, converting each respective box into a respective patch, feeding each one of a plurality of patches into a patch classifier implemented as a convolutional neural network (CNN) trained on a second training dataset that includes patches extracted from the ground truth box labels of the first training dataset, wherein a respective patch score obtained from the patch classifier for a respective patch corresponds to a respective box score obtained from the detector component from a respective box corresponding to the respective patch, obtaining as an outcome of the patch classifier, a plurality of patch scores, each respective patch associated with a respective patch score indicative of likelihood of the visual finding being depicted therein, computing a dot product of the plurality of box scores and the plurality of patch scores, and providing the dot product as an image-level indication of likelihood of the visual finding being depicted in the medical image.

According to a second aspect, a computer implemented method of creating a two-stage detector ML model for identifying a visual finding in a target medical image, comprises: accessing a first training dataset including a plurality of medical images annotated with ground truth boxes depicting the visual finding therein, training a detector component using the first training dataset for generating, in response to an input of the target medical image, an outcome of a plurality of boxes and a plurality of box scores each indicative of likelihood of the visual finding being depicted in a respective box, accessing a second training dataset that includes patches extracted from the ground truth box labels of the first training dataset, the patches labelled with the ground truth corresponding to the box labels, training a patch classifier component using the second training dataset for generating, in response to an input of a plurality of patches obtained from the plurality of boxes generated by the detecting component, a plurality of patch score, each respective patch associated with a respective patch score indicative of likelihood of the visual finding being depicted therein, and providing the two-stage detector ML model, comprising of: the detector component, the patch classifier, and code for computing a dot product of the plurality of box scores and the plurality of patch scores, wherein the two-stage detector ML model generates the dot product as an image-level indication of likelihood of the visual finding being depicted in an input target medical image.

In a further implementation of the first, and second aspects, the detector component generates at least 50 boxes.

In a further implementation of the first, and second aspects, boxes having highest box scores are provided as the plurality of boxes.

In a further implementation of the first, and second aspects, further comprising: duplicating the plurality of box scores, performing an image processing operation on each of the plurality of boxes to generate a double of the plurality of boxes, wherein converting comprises converting the double of the plurality of boxes to a double of the plurality of patches, wherein feeding comprises feeding the double of the plurality of patches, wherein a double of the plurality of patch scores is obtained as the outcome of the patch classifier, wherein computing the dot product comprising computing the dot product of the duplicated plurality of box scores and the double of the plurality of patch scores.

In a further implementation of the first, and second aspects, the detector component is trained on the first training dataset that includes for each medical image annotated with the ground truth box label, an indication of a category selected from a plurality of categories for the visual finding, wherein the plurality of boxes and the plurality of box scores are for the plurality of categories, wherein the patch classifier is trained on the second training dataset that includes patches extracted from the ground truth boxes of the first training dataset, each labelled with a single indication denoting all of the plurality of categories of the first training dataset.

In a further implementation of the first, and second aspects, further comprising: feeding a plurality of sample medical images labelled with a ground truth negative label and excluded from the first training dataset, into the detector component, to obtain an outcome of a plurality of boxes denoting negatives, extracting the plurality of boxes denoting negatives as a plurality of negative patches, adding the plurality of negative patches labelled with an indication of negative to the second training dataset.

In a further implementation of the first, and second aspects, further comprising: feeding a plurality of sample medical images labelled with a ground truth positive label into the detector component, to obtain an outcome of a plurality of boxes denoting positive, extracting the plurality of boxes denoting positive as a plurality of positive patches, adding the plurality of positive patches labelled with an indication of positive to the second training dataset.

In a further implementation of the first, and second aspects, further comprising selecting a subset of the plurality of boxes denoting positive having an overlap over a threshold of intersection over union (IOU) with the ground truth box label.

In a further implementation of the first, and second aspects, an equal number of boxes and corresponding box scores are generated for each category of the plurality of categories In a further implementation of the first, and second aspects, the first training dataset includes mammographic images depicting a plurality of views of left and right breasts, and the category is selected from soft lesion and calcification.

In a further implementation of the first, and second aspects, the dot product indicates likelihood of breast cancer, and further comprising treating a subject for breast cancer using a treatment effective for breast cancer, selected from a group consisting of: biopsy, radiation therapy, chemotherapy, immunotherapy, surgical excision, and combinations of the aforementioned.

In a further implementation of the first, and second aspects, further comprising feeding the medical image into a whole image classifier component trained on a whole image classifier training dataset of a plurality of sample medical images of a plurality of subjects each labelled with an indication of positive or negative, obtaining a whole image classifier score as an outcome of the whole image classifier component, and obtaining a medical image level score by aggregating the whole image classifier score and the dot product into a single value.

In a further implementation of the first, and second aspects, the whole image classifier component is designed for fast inference and high specificity of a binary classification task in large grayscale medical images, the whole image classifier component implemented with a number of trainable parameters less than about 150000, wherein a plurality of layers are compacted.

In a further implementation of the first, and second aspects, further comprising: feeding the medical image into each of a plurality of detector components trained using different initialization values to obtain a plurality of dot products, feeding the medical image into each of a plurality of whole image classifier components trained using different initialization values to obtain a plurality of classification scores, and obtaining the medical image level score by aggregating the plurality of dot products and the plurality of whole image classifier scores into the single value.

In a further implementation of the first, and second aspects, each medical image comprises a set of four mammographic images including two images for a left side and two images for a right side, wherein a respective classification score is computed by computing a respective mammographic image score for each of the four mammographic images, computing a maximum mammographic image score of a mean mammographic image score for the left side and a mean mammographic image score for the right side, wherein the maximum mammographic image score is provided as the respective classification score.

In a further implementation of the first, and second aspects, further comprising computing a plurality of augmentation sets for the set of four mammographic images, wherein a respective maximum mammographic image score is computed for each of the plurality of augmentation sets, computing a mean of a plurality of the maximum mammographic images scores, and providing the mean as respective classification.

In a further implementation of the first, and second aspects, the indication of positive includes: positive due to a plurality of sub-categories, benign, and one of the plurality of sub-categories defined as positive, wherein the whole image classifier component is trained using the training dataset for outputting a value for each of a plurality of categories consisting of: positive due to a plurality of sub-categories, benign, one of the plurality of sub-categories defined as positive, and wherein obtaining the whole image classifier score as the outcome of the whole image classifier component comprises obtaining a target value for the category of positive due to the plurality of sub-categories, and discarding other target values of other categories.

In a further implementation of the first, and second aspects, each image is a whole high resolution mammographic image selected from a group consisting of left craniocaudal (LCC), left mediolateral oblique (LMLO), right craniocaudal (RCC), and right mediolateral oblique (RMLO) having resolution at least greater than 1840×1840, wherein the plurality of sub-categories are selected from a group consisting of: malignant calcification, and soft lesion.

In a further implementation of the first, and second aspects, further comprising providing an ensemble of ML models by: training a whole image classifier component by: accessing a whole image classifier training dataset of a plurality of sample medical images of a plurality of subjects each labelled with an indication of positive or negative, training the whole image classifier component for generating a whole image classifier score as an outcome in response to an input of the target medical image, and providing a ML model ensemble comprising: a plurality of two-stage detector components trained using different initialization values that generate a plurality of dot products in response to an input of the target image, a plurality of whole image classifier components trained using different initialization values that generate a plurality of classification scores in response to the input of the target image, and code that computes a medical image level score by aggregating the plurality of dot products and the plurality of whole image classifier scores into a single value.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 7 is a table summarizing training data of mammographic studies, in accordance with some embodiments of the present invention;

FIG. 8 is a table summarizing categories into which the remaining studies in all partitions were divided into, in accordance with some embodiments of the present invention;

FIG. 9 is a table summarizing training data used in the experiment, in accordance with some embodiments of the present invention.

DESCRIPTION OF SPECIFIC EMBODIMENTS OF THE INVENTION

Figure 1:
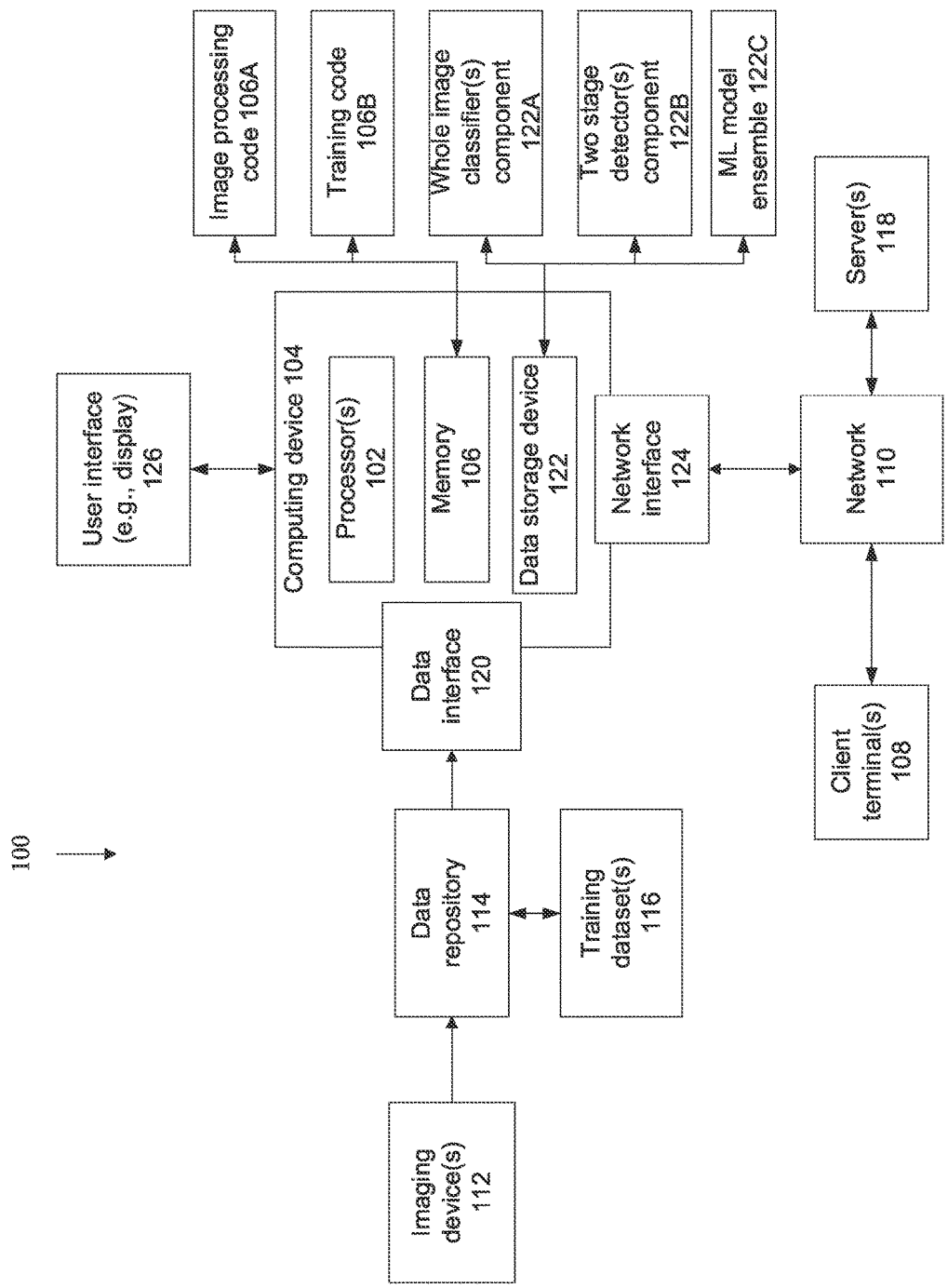
FIG. 1 is a block diagram of a system for creating a two-stage ML detector and/or whole image classifier and/or ensemble including one or more of the two-stage ML detectors and one or more of the whole image classifiers, for identifying likelihood of a visual finding in a target medical image, and/or for inference of the target medical image by the two-stage ML detector and/or whole image classifier and/or ensemble, in accordance with some embodiments of the present invention.

The present invention, in some embodiments thereof, relates to machine learning models and, more specifically, but not exclusively, to systems and method for training machine learning models to identify visual finding(s) in medical images, and inference by the trained machine learning models.

As aspect of some embodiments of the present invention relates to systems, methods, an apparatus, and/or code instructions (stored on a memory and executable by one or more processors) for identifying one or more visual findings in a medical image by a trained two-stage detector, for example, identifying an indication of cancer in mammographic images. The two-stage detector includes a detector component implemented a machine learning (ML) model (e.g., neural network) and a patch classifier implemented as a convolutional neural network (CNN). The detector component is trained on a first training dataset of a medical images annotated with ground truth boxes depicting a visual finding therein. The patch classifier is trained on a second training dataset that includes patches extracted from the ground truth box labels of the first training dataset and labelled with ground truth labels of the boxes labels of the boxes corresponding to the patches. The medical image is fed into the detector component. An outcome of boxes of the medical image is obtained from the detector component. Each respective box is associated with a respective box score indicative of likelihood of the visual finding being depicted therein. The detector may be configured to output a large number of boxes, for example, over 10, 20, 50, 100, or other numbers. Each respective box is converted into a respective patch, for example, by resizing each respective box to a common patch size format. Each one of the patches is fed into a patch classifier. An outcome of a respective patch score indicative of likelihood of the visual finding being depicted in the respective patch, is obtained for each patch from the patch classifier. Each respective patch score obtained from the patch classifier for a respective patch corresponds to a respective box score obtained from the detector component from a respective box corresponding to the respective patch. A dot product of the box scores and the corresponding patch scores is computed. The dot product is provided as an image-level indication of likelihood of the visual finding being depicted in the medical image.

As aspect of some embodiments of the present invention relates to systems, methods, an apparatus, and/or code instructions (stored on a memory and executable by one or more processors) for creating a two-stage detector ML model for identifying a visual finding in a target medical image. The two-stage detector includes a detector component and a patch classifier component. The detector component is created by accessing a first training dataset including a medical images annotated with ground truth boxes depicting the visual finding therein. The detector component is trained using the first training dataset for generating, in response to an input of the target medical image, an outcome of multiple boxes and respective box scores each indicative of likelihood of the visual finding being depicted in a respective box. The detector may be configured to output a large number of boxes, for example, over 10, 20, 50, 100, or other numbers. The patch classifier component is created by accessing a second training dataset that includes patches extracted from the ground truth box labels of the first training dataset. The patches are labelled with the ground truth corresponding to the box labels. It is noted that patches indicating a ground truth of lack of visual finding depicted therein may be obtained from images where no visual finding is depicted. The patch classifier component is trained using the second training dataset for generating, multiple patch scores in response to an input of patches obtained from the boxes generated by the detecting component. Each respective patch is associated with a respective patch score indicative of likelihood of the visual finding being depicted therein. The two-stage detector ML model is provided. The two-stage detector includes the detector component, the patch classifier, and code for computing a dot product of the box scores and the patch scores. The two-state detector ML model generates the dot product as an image-level indication of likelihood of the visual finding being depicted in an input target medical image.

At least some implementations of the systems, methods, apparatus, and/or code instructions described herein address the technical problem of increasing accuracy of a machine learning model, such as a classifier and/or detector, identifying a visual finding (e.g., breast cancer) in a medical image (e.g., mammogram). At least some implementations of the systems, methods, apparatus, and/or code instructions described herein improve the technical field of machine learning (ML) models, in particular, classifiers and/or detectors, such as neural network architectures, by increasing the accuracy of the classifier and/or detector in identifying a visual finding in a medical image, optionally finding an indication of breast cancer in a mammographic image. Due to the nature of medical images, visual findings that are clinically significant (e.g., cancer) are difficult to identify in comparison to, for example, other background anatomical features, artifacts, and benign features. The background may be a dense homogenous looking pattern, and the visual finding may be extremely subtle and/or smaller. The accuracy may be increased by reducing false positives and/or false negatives, and/or by increasing sensitivity and/or increasing specificity. A higher accuracy may reduce the number of visual findings found by the classifier that are benign, which may avoid or reduce performing biopsies on the benign findings. A higher accuracy may increase the number of otherwise difficult to find visual findings that are cancerous, and that may be missed. The classifier and/or detector may identify a smaller and more accuracy set of medical images for further review by a radiologist.

In at least some implementations, the improvement of an increase in accuracy of the detector and/or classifier is obtained by a two-stage detector architecture that includes a detector component and a classifier component. The medical image is fed into the detector component to obtain multiple boxes relative to the image (e.g., overlaid on the image, defined as coordinates relative to the image), each representing a likelihood of a visual finding being depicted therein. Each box is associated with a respective box score indicating likelihood of the visual finding being depicted therein. Inventors discovered that higher image-level identification may be obtained when the number of boxes is much large than is usually derived in standard approaches. For example, standard detectors may generate a small number of boxes, for example, 0-5, or 2-3 boxes. In at least some implementations described herein, the number of generated boxes is large, for example, greater than 10, 25, 50, 100, or larger numbers. Each box is converted into a patch, which is then fed into a patch classifier to obtain a respective patch score indicating likelihood of the visual finding being depicted in the respective patch. A dot product is computed between the box scores and corresponding patch scores. The dot product denotes the image-level likelihood of the visual finding being depicted in the medical image. Inventors discovered that computing the dot product between the box scores and patch scores, optionally for a large number of patches, increases accuracy of the image-level likelihood of identifying the visual finding in the medical image.

Breast cancer is the most commonly occurring cancer in women and the second most common cancer overall. In the first decade of the 20th century, breast cancer accounted for about half of all deaths in the United States. By 1955, breast cancer had risen as a cancer of concern to more than a third of women and now makes up 5% of all cancer deaths. Breast cancer was responsible for 40% of all deaths in 2005. It is one of the most dangerous cancers—about three-quarters of all breast cancers are breast cancer. One in five women will develop breast cancer within their lifetime. Breast cancer can be broadly categorized into two main categories, in situ cancer and invasive or infiltrating cancer. In situ breast cancer (ductal carcinoma in situ or DCIS) is further sub-classified as either ductal (Ductal carcinoma in situ (DCIS)) or lobular carcinoma in situ (LCIS). LCIS is not considered as cancer but increases a person's risk of developing invasive breast cancer later on in life. Similar to in situ cancers, invasive cancers are a heterogeneous group of tumors differentiated into histological subtypes, invasive breast cancer accounts for approximately 70% of cancers detected with digital screening mammographic examinations. The major invasive tumor types include: infiltrating ductal carcinoma (IDC), invasive lobular carcinoma (ILC), mucinous (colloid), tubular, medullary and papillary carcinomas. Invasive ductal carcinoma (IDC) is the most common form of invasive breast cancer. It accounts for 55% of breast cancer incidence upon diagnosis. The majority of women with breast cancer are diagnosed in the late stages and the overall five-year survival rate is very low, with a range of 10-40%. On the other hand, the five-year survival rate for early localized breast cancer exceeds 80%, therefore early diagnosis is critical. Breast cancer screening for early detection have shown to decrease mortality due to breast cancer in 20-25%. Breast screening is done in several techniques using different technologies, the most prevalent method used worldwide being x-ray imaging studies, called mammography. Mammography studies are performed by compressing the breasts in a dedicated machine during the exposure to X-rays. The studies are called mammograms and they include four standard X-ray views, two for each breast. The classical mammograms are two dimensional (2D) and are referred to as "normal mammograms", 2D mammograms, DM—for digital mammogram or FFDM: Full Field Digital Mammograms. In recent years Breast Tomosynthesis has also started to be used as a screening tool, mainly in the US. Tomosynthesis, a.k.a DBT—Digital Breast Tomosynthesis or 3D Mammography—is a partial tomography for breast that is performed in a process that resembles a CT (computerized tomography).

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
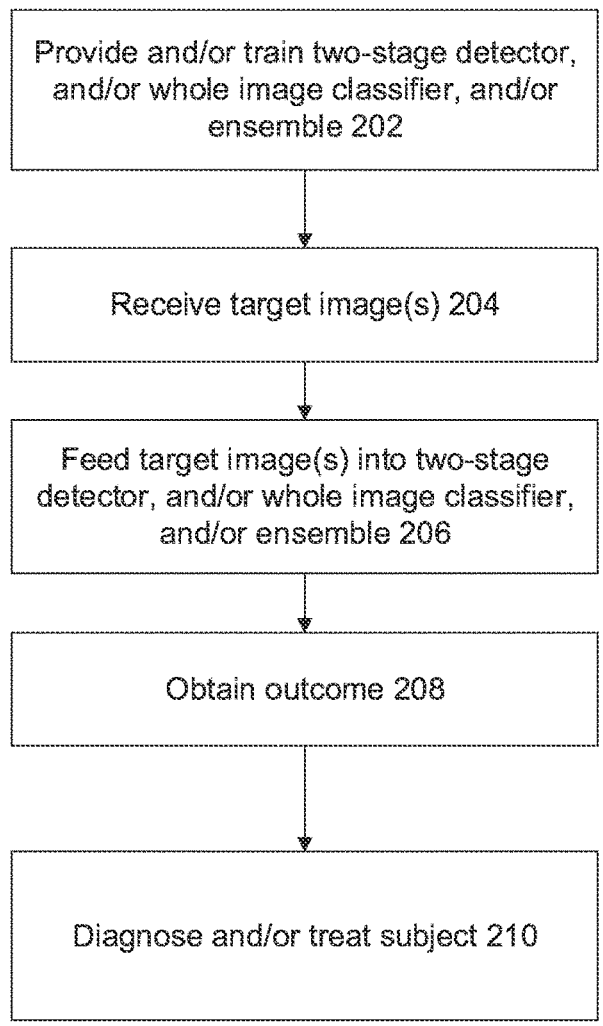
FIG. 2 is a flowchart of a method of inference of a target medical image by the two-stage ML detector and/or whole image classifier and/or ensemble for identifying likelihood of a visual finding in the target medical image, in accordance with some embodiments of the present invention.
Figure 3:
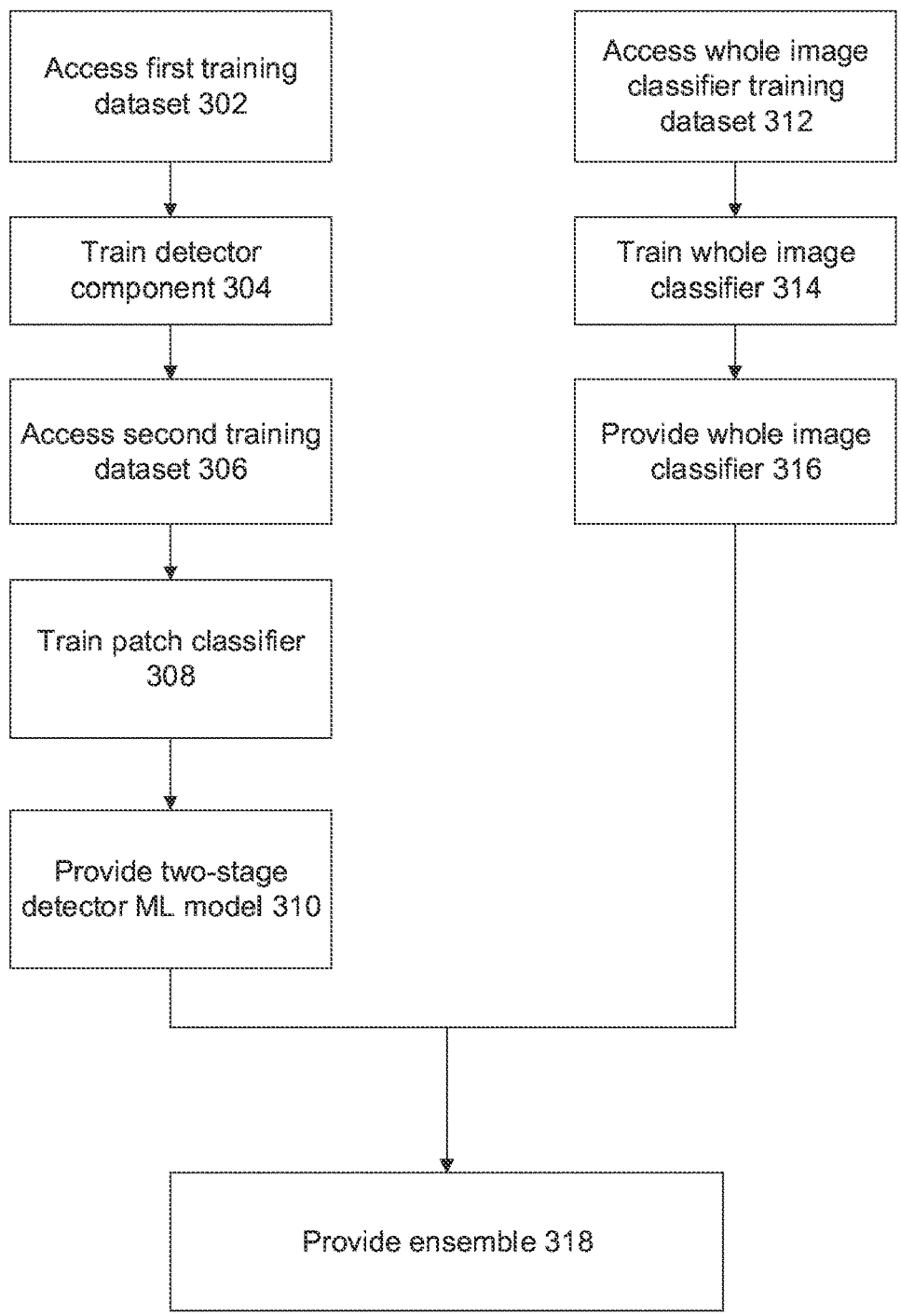
FIG. 3 is a flowchart of a method of creating a two-stage ML detector and/or whole image classifier and/or ensemble including one or more of the two-stage ML detectors and one or more of the whole image classifiers, for identifying likelihood of a visual finding in a target medical image, in accordance with some embodiments of the present invention.
Figure 4:
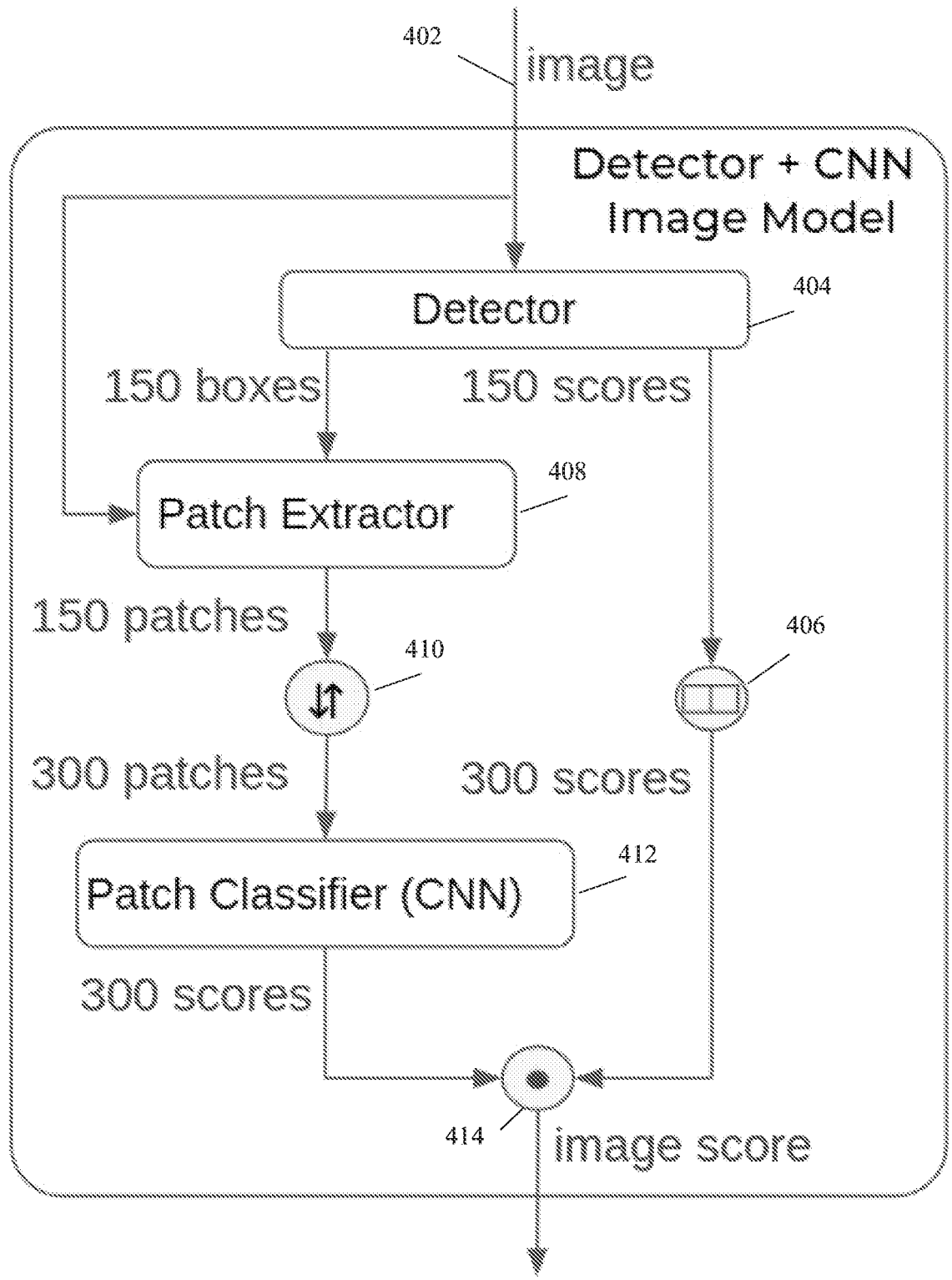
FIG. 4 is a flowchart of a method of identifying a visual finding in a medical image using a two-stage detector, in accordance with some embodiments of the present invention.
Figure 5:
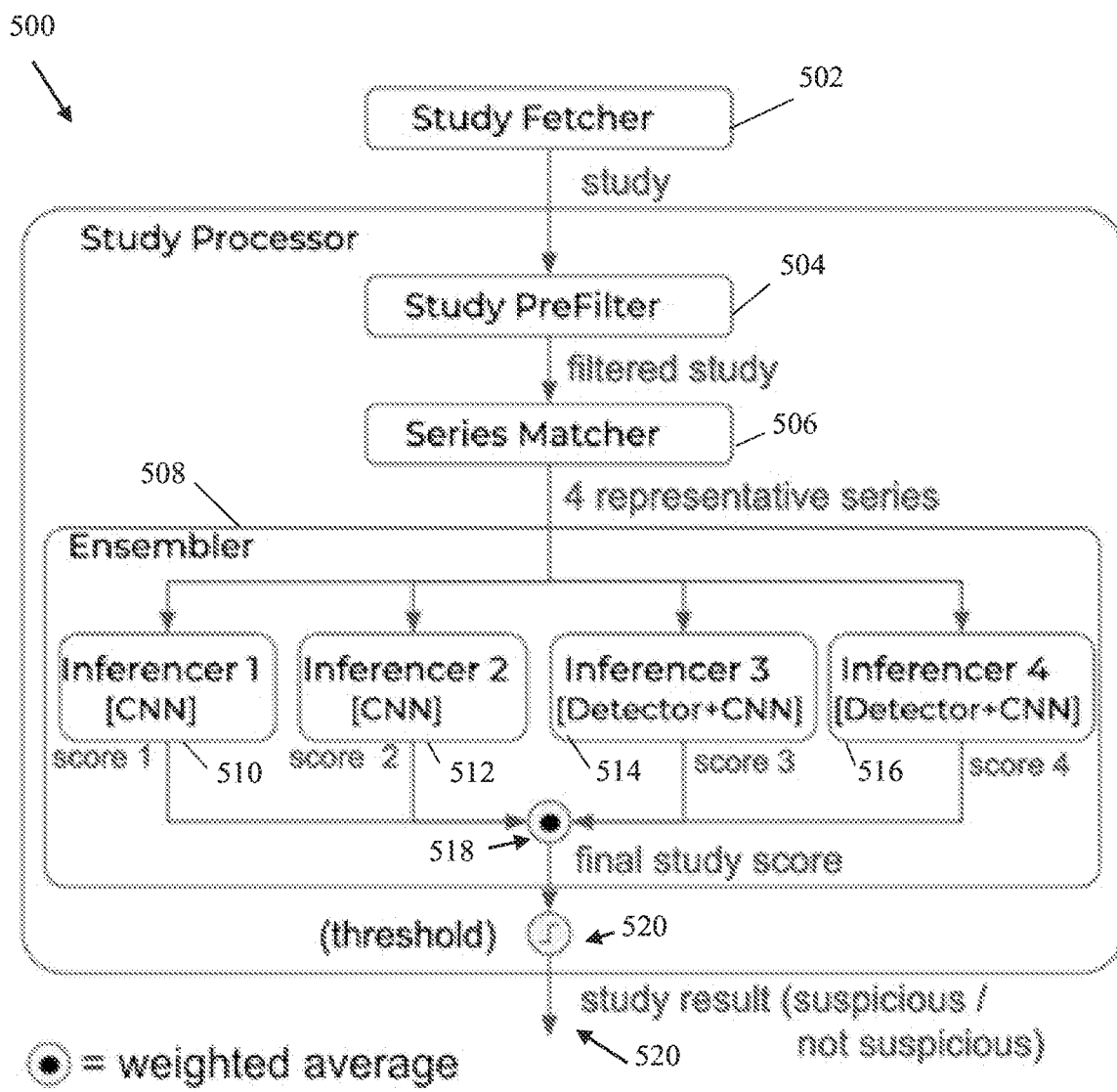
FIG. 5 is a flowchart of a method of computing an image-level score for a target medical image using an ensemble that includes one or more two-stage ML detectors and one or more whole image classifiers, in accordance with some embodiments of the present invention.
Figure 6:
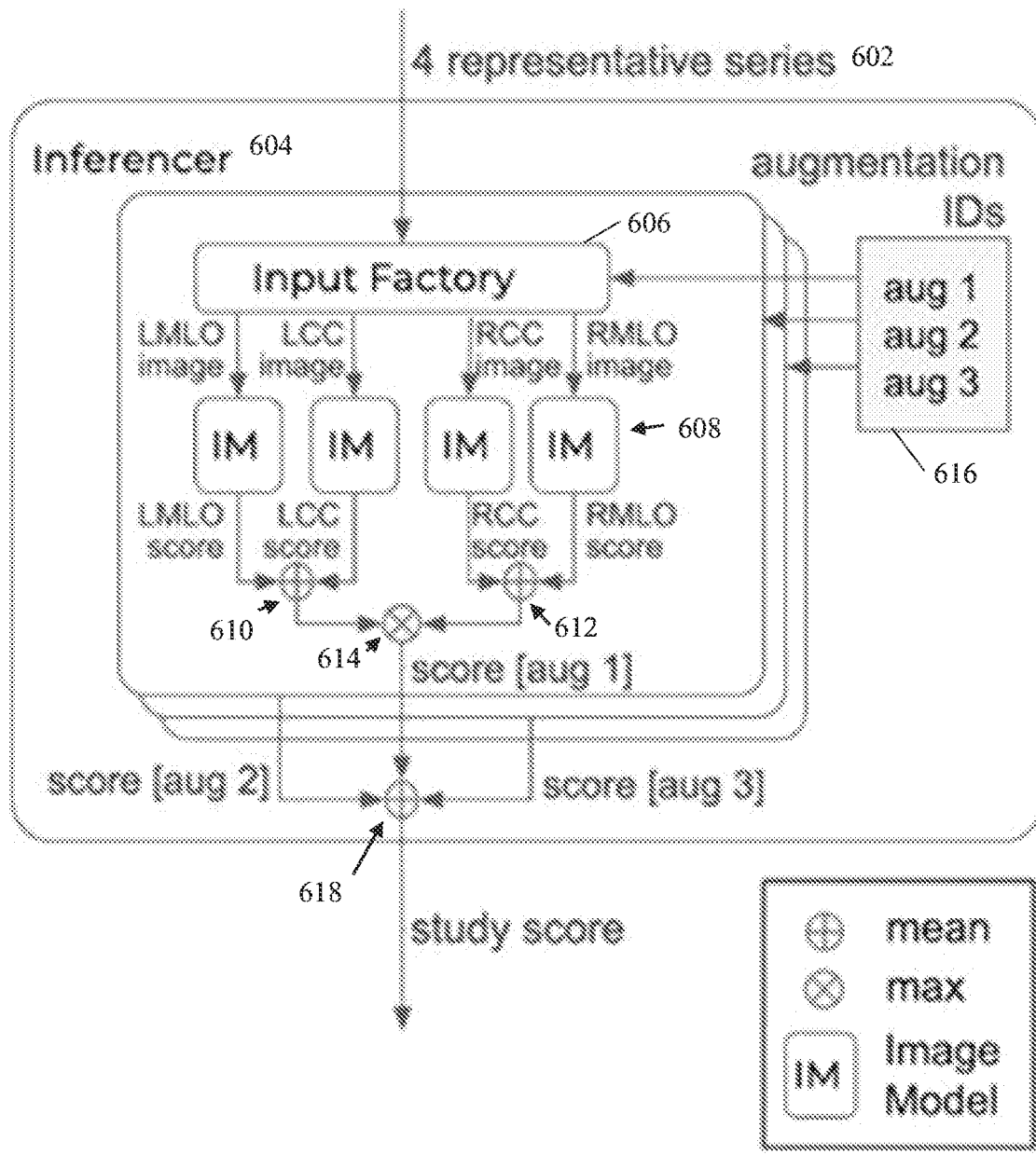
FIG. 6 is a flowchart of a method of test time augmentation for one or more of the two-stage ML detectors and/or whole image classifiers which may be fed multiple images of a series, optionally of the ensemble, in accordance with some embodiments of the present invention.

Reference is now made to FIG. 1, which is a block diagram of a system for creating a two-stage ML detector and/or whole image classifier and/or ensemble including one or more of the two-stage ML detectors and one or more of the whole image classifiers, for identifying likelihood of a visual finding in a target medical image, and/or for inference of the target medical image by the two-stage ML detector and/or whole image classifier and/or ensemble, in accordance with some embodiments of the present invention. Reference is now made to FIG. 2, which is a flowchart of a method of inference of a target medical image by the two-stage ML detector and/or whole image classifier and/or ensemble for identifying likelihood of a visual finding in the target medical image, in accordance with some embodiments of the present invention. Reference is also made to FIG. 3, which is a flowchart of a method of creating a two-stage ML detector and/or whole image classifier and/or ensemble including one or more of the two-stage ML detectors and one or more of the whole image classifiers, for identifying likelihood of a visual finding in a target medical image, in accordance with some embodiments of the present invention. Reference is also made to FIG. 4, which is a flowchart of a method of identifying a visual finding in a medical image using a two-stage detector, in accordance with some embodiments of the present invention. Reference is also made to FIG. 5, which is a flowchart of a method of computing an image-level score for a target medical image using an ensemble that includes one or more two-stage ML detectors and one or more whole image classifiers, in accordance with some embodiments of the present invention. Reference is also made to FIG. 6, which is a flowchart of a method of test time augmentation for one or more of the two-stage ML detectors and/or whole image classifiers which may be fed multiple images of a series, optionally of the ensemble, in accordance with some embodiments of the present invention.

System 100 may implement the acts of the method described with reference to FIGS. 2-6, optionally by a hardware processor(s) 102 of a computing device 104 executing code instructions stored in a memory 106.

Computing device 104 may be implemented as, for example, a client terminal, a server, a virtual server, a radiology workstation, a virtual machine, a computing cloud, a mobile device, a desktop computer, a thin client, a Smartphone, a Tablet computer, a laptop computer, a wearable computer, glasses computer, and a watch computer. Computing 104 may include an advanced visualization workstation that sometimes is add-on to a radiology workstation and/or other devices for presenting indications of the identified visual findings and/or other computer added detections to the radiologist.

Computing device 104 may include locally stored software that performs one or more of the acts described with reference to FIGS. 2-6, and/or may act as one or more servers (e.g., network server, web server, a computing cloud, virtual server) that provides services (e.g., one or more of the acts described with reference to FIGS. 2-6) to one or more client terminals 108 (e.g., remotely located radiology workstations, remote picture archiving and communication system (PACS) server, remote electronic medical record (EMR) server) over a network 110, for example, providing software as a service (SaaS) to the client terminal(s) 108, providing an application for local download to the client terminal(s) 108, as an add-on to a web browser and/or a medical imaging viewer application, and/or providing functions using a remote access session to the client terminals 108, such as through a web browser.

Different architectures based on system 100 may be implemented. In one example, computing device 104 provides centralized services. Training of the ML model ensemble and/or components, i.e., classifier component and/or detector component, is performed centrally by computing device 104, as described herein. Inference may be centrally performed by computing device 104. Alternatively, training is performed by another computing device, and inference is centrally performed by computing device 104. Images may be provided to computing device 104 for centralized inference by the trained ML model ensemble and/or components, i.e., classifier component and/or detector component. Images may be provided to computing device 104, for example, via an API, a local application, and/or transmitted using a suitable transmission protocol. The outcome of the inference may be provided, for example, to client terminal(s) 108 for presentation on a display and/or local storage, stored in an electronic medical record (e.g., hosted by server 118), and/or stored by computing device 104. In another example, computing device 104 provides centralized training of the ML model ensemble and/or components, using different training datasets provided by different client terminals 108 and/or servers 118. For example, training datasets originating from different hospitals, and/or training dataset for different imaging modalities, and/or for different body regions. Respective generated ML model ensembles and/or components may be provided to the corresponding remote devices (e.g., client terminal(s) 108 and/or server(s) 118) for local use. For example, each hospital uses the ML model ensemble and/or components created from their own training dataset for evaluation of new images captured at the respective hospital, and/or different ML model ensembles and/or components are locally used to evaluate different medical images generated by different imaging modalities, such as mammography, x-ray, and ultrasound.

Imaging device 112 provides the images, which may be included in training dataset(s) 116 and/or for inference. Image device 112 may include a 2D, 3D, and/or 4D imaging device. 3D and/or 4D images may be converted to 2D images for inference, for example, by selecting 2D slices from a 3D scan, and/or converting the 3D image into a 2D image such as by maximum pixel intensity (MPI) and/or approaches described herein. Imaging devices 112 may be implemented as, for example, a 2D mammography device, breast tomography (i.e., 3D mammography device), 3D ultrasound, nuclear imaging device such as PET, colonoscope, bronchoscope, endoscope, 2D ultrasound, an x-ray machine, a magnetic resonance imaging (MRI) device, and/or a computer tomography (CT) machine.

Training dataset(s) 116 may be stored in a data repository 114, for example, a storage server, a computing cloud, virtual memory, and a hard disk. Training dataset(s) 116 are used to train the ML model ensembles and/or components, as described herein. It is noted that training dataset(s) 116 may be stored by a server 118, accessibly by computing device 104 over network 110.

Computing device 104 may receive the training dataset(s) 116 from imaging device 112 and/or data repository 114 using one or more data interfaces 120, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 102 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 102 may include one or more processors (homogenous or heterogeneous), which may be arranged for parallel processing, as clusters and/or as one or more multi core processing units.

Memory 106 (also referred to herein as a program store, and/or data storage device) stores code instruction for execution by hardware processor(s) 102, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, memory 106 may store image processing code 106A that implement one or more acts and/or features of the method described with reference to FIGS. 2, 4, 5, and 6 and/or training code 106B that execute one or more acts of the method described with reference to FIG. 3.

Computing device 104 may include a data storage device 122 for storing data, for example, a trained whole image classifier component 122A, a trained two-stage detector component 122B, a trained ML model ensemble 122C which includes multiple whole image classifier components and/or two-stage detector components, and/or training dataset(s) 116. Data storage device 122 may be implemented as, for example, a memory, a local hard-drive, a removable storage device, an optical disk, a storage device, and/or as a remote server and/or computing cloud (e.g., accessed over network 110). It is noted that components 122A-B and/or ensemble 122C and/or training dataset(s) 116 may be stored in data storage device 122, with executing portions loaded into memory 106 for execution by processor(s) 102.

Computing device 104 may include a network interface 124 for connecting to network 110, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 104 may access one or more remote servers 118 using network 110, for example, to obtain and/or provide training dataset(s) 116, an updated version of image processing code 106A, training code 106B, and/or the trained components 122A-B and/or trained ensemble 122C.

It is noted that data interface 120 and network interface 124 may exist as two independent interfaces (e.g., two network ports), as two virtual interfaces on a common physical interface (e.g., virtual networks on a common network port), and/or integrated into a single interface (e.g., network interface). Computing device 104 may communicate using network 110 (or another communication channel, such as through a direct link (e.g., cable, wireless) and/or indirect link (e.g., via an intermediary computing device such as a server, and/or via a storage device) with one or more of:

Client terminal(s) 108, for example, when computing device 104 acts as a server providing image analysis services (e.g., SaaS) to remote radiology terminals, for analyzing remotely obtained anatomical images using the trained components 122A-B and/or trained ensemble 122C.

Server 118, for example, implemented in association with a PACS, which may store training dataset(s) 116 and/or may store captured images for inference.

Imaging device 112 and/or data repository 114 that store images acquired by imaging device 112. The acquired images may be fed into trained components 122A-B and/or trained ensemble 122C for inference thereof.

Computing device 104 and/or client terminal(s) 108 and/or server(s) 118 include and/or are in communication with a user interface(s) 126 that includes a mechanism designed for a user to enter data (e.g., patient data) and/or view the outcome of the inference of the captured image(s), for example indications of identified visual findings. Exemplary user interfaces 126 include, for example, one or more of, a touchscreen, a display, a keyboard, a mouse, and voice activated software using speakers and microphone.

Referring now back to FIG. 2, at 202, a two-stage detector and/or a whole image classifier, and/or ensemble that includes one or more two-stage detectors and/or one or more whole image classifiers, is provided and/or trained.

An exemplary training process is described with reference to FIG. 3.

At 204, one or more target images are received. The target images are medical images, depicting an interior of a body of the subject. The target images may be 2D images, or 2D data extracted from 3D data (e.g., slices of a CT scan, aggregated data such as by computing maximal pixel intensity (MIP) for a 3D volume, and the like). The target images may be anatomical images depicted by an anatomical imaging modality, for example, CT, MRI, mammography, x-ray, ultrasound.

The target images may be mammographic images for identification of breast cancer and/or abnormalities depicted therein. The target images may include a series of multiple images, for example, a mammographic series of image that includes two or more images for each side, for example, left craniocaudal (LCC), left mediolateral oblique (LMLO), right craniocaudal (RCC), and right mediolateral oblique (RMLO). Other images for detection of other findings may be used, for example, chest x-rays and/or slices of a chest CT for detection of pulmonary nodules.

At 206, the target images are fed into the two-stage detector and/or whole image classifier and/or ensemble. Exemplary processes of feeding the image(s) are described with reference to FIGS. 4-6.

At 208, an outcome indicative of likelihood of the visual feature depicted therein is obtained. The outcome may be per image (i.e., image-level), and/or for the series of images as a whole (i.e., series-level).

At 210, the subject may be diagnosed and/or treated according to the indication, and/or other action may be taken.

Optionally, a user visually inspects the region of the mammographic image identified as likely depicting the visual finding, optionally breast cancer.

Optionally, a diagnosis of breast cancer (or other diagnosis based on the likelihood of the visual finding being depicted therein) is made, manually by a user and/or automatically by a computer. The diagnosis may be stored, for example, in an electronic medical record (EMR) of the subject, and/or presented on a display.

Optionally, the subject is treated for the diagnosis, for example, for breast cancer and/or other cancers, using a treatment effective for breast cancer and/or other cancers. Exemplary treatments include: biopsy, radiation therapy, chemotherapy, immunotherapy, surgical excision, and combinations of the aforementioned.

Referring now back to FIG. 3, at 302-310, a two-stage detector is trained. At 302-304, the detector component of the two-stage detector is trained, and at 306-308 the patch classifier component of the two-stage detector is trained.

The detector component and/or the patch classifier component may be implemented as neural networks.

An exemplary training dataset and training approach based on 302-306 is now described.

At 302, a first training dataset that includes medical images annotated with ground truth boxes depicting visual finding therein is accessed. The first training dataset may be created by users manually marking boxes around visual findings identified by the users.

It is noted that the term box is exemplary and not necessarily limiting, and other marking may be used, for example, circles, arrows, and irregular borders.

The medical images may be mammographic images, optionally arranged as a series of 4 standard view mammographic images of the left and/or right side (e.g., 2 views per side).

At 304, a detector component is trained using the first training dataset. The detector component generates, in response to an input of the target medical image, an outcome of multiple boxes, each box with a respective box score indicative of likelihood of the visual finding being depicted therein. The boxes may be of varying sizes and/or of fixed sizes.

Optionally, the detector component is configured to generate a large number of boxes, larger than standard detector settings, for example, at least 10, or 25, or 50, or 100, or 150, or 200, or 250, or other values. As described herein, Inventors discovered that the large number of boxes increase the accuracy of detecting visual findings depicted in the medical images.

At 306, a second training dataset is accessed and/or created, optionally automatically. The second training dataset includes patches extracted from the ground truth box labels of the first training dataset. The patches may be the boxes of the first training dataset. The boxes, which may be of varying sizes, may be converted (e.g., resized) to a common patch size format. Each patch is labelled with the ground truth corresponding to the box labels of the box used to create the patch.

At 308, a patch classifier component is trained using the second training dataset for generating, in response to an input of a patch, a patch score indicative of likelihood of the visual finding being depicted in the inputted patch.

During inference, each box generated by the detecting component is converted into a patch. Each patch is fed into the patch classifier to obtain a patch score corresponding to the box score of the box used to create the inputted patch.

The patch classifier may be trained using a binary cross-entropy loss function.

At 310, the two-stage detector ML model is provided. The two-stage detector ML model includes the following components: the detector component, the patch classifier, and code for computing a dot product of the box scores (outcomes of the detector component) and the patch scores (outcomes of the patch classifier in response to input of patches created from boxes generated by the detector component). The two-state detector ML model generates the dot product as an image-level indication of likelihood of the visual finding being depicted in an input target medical image Multiple two-stage detector components may be created, for example, using different initialization weights of the neurons, for example, randomly setting the weights.

Optionally, different training approaches based on 302-308 may be implemented. One or more of the following exemplary approaches may be implemented:

The first training dataset (used to train the detector component) may include, for each medical image annotated with a ground truth box label, an indication of a category for the visual finding selected from multiple categories. Each box may be labeled with a respective category. Exemplary categories include soft lesion, calcification, and benign. The multiple boxes and associated box scores generated by the detector component are for the multiple categories. Optionally, an equal number of boxes and corresponding box scores are generated for each category, for example, 75 boxes for soft lesion, and 75 boxes for calcification. The second training dataset (used to train the patch classifier) includes patches extracted from the ground truth boxes of the first training dataset. Each patch is labelled with a single indication denoting all of the categories of the first training dataset.

Multiple sample medical images each labelled with a ground truth negative label (representing negative findings and not annotated with boxes) are fed into the detector component. The sample medical images are excluded from the first training dataset. The detector component generates an outcome of multiple boxes, where each box indicates a negative visual finding (i.e., no visual finding depicted in the boxes). The boxes indicating negatives are extracted as negative patches. The negative patches are labelled with an indication of negative, and added to the second training dataset. The patch classifier is trained on the second training dataset with negative patches.

Multiple sample medical images each labelled with a ground truth positive label (representing positive visual findings depicted therein) are fed into the detector component, to obtain an outcome of boxes denoting positive visual findings. Optionally, a subset of the boxes denoting positive are selected. Boxes outputted by the detector that have an overlap over a threshold of intersection over union (IOU) with the ground truth box label may be selected as part of the subset. The threshold may be, for example, 60%, 70%, 75%. 80%, 85%, 90%, 95%, 96%, 97%, 98%, 99%, and other values. Positive patches are extracted from the (selected subset of) positive boxes. The positive patches each labelled with an indication of positive are included in the second training dataset.

Features 312-316 describe a process of training the whole image classifier component. The whole image classifier component may be implemented as a neural network.

At 312, a whole image classifier training dataset is accessed and/or created. The whole image classifier training dataset includes sample medical images of multiple subjects, where each respective training image labelled with an indication of positive or negative for the visual finding. The positive findings may be, and/or may include sub-categories, for example, malignant calcification and soft lesion.

Each image may be a whole high resolution image, having a resolution dimension of at least 1000, or 1500, or 1840, or greater, for example, 1840×1840.

Images may be whole high resolution mammographic image, including LCC, LMLO, RCC, and RMLO.

At 314, the whole image classifier is trained on the whole image classifier training dataset. The whole image classifier component generates a whole image classifier score as an outcome in response to an input of the target medical image. The whole image classification score may be, for example, a classification category (e.g., positive, negative; or malignant calcification, soft lesion, and negative) and/or a value (e.g., probability between 0-1) of likelihood of a positive finding.

Multiple whole image classifiers may be created, for example, using different initialization weights for neurons. The initialization weights may be set randomly.

The whole image classifier may be trained using a multi-task training framework, to generate an indication of positive when one of the following exemplary classification outcomes is obtained: positive due to multiple sub-categories (e.g., positive for any reason), benign, and one of the sub-categories defined as positive. The training dataset may include images labelled with the exemplary classification outcomes of multiple sub-categories indicating positive, positive (due to one of the multiple sub-categories) and benign. The whole image classifier component may be trained using the training dataset for outputting a value for each of the categories, i.e., positive due to a plurality of sub-categories, benign, one of the plurality of sub-categories defined as positive. During inference, a whole image classifier score is obtained as the outcome of the whole image classifier component by obtaining a target value for the category of positive due to the multiple sub-categories, and discarding other target values of other categories.

Inventors discovered that the multi-task training framework improves the performance of the desired outcome, and speeds up convergence.

For example, the whole image classifier may be trained to output 4 predictions (each with a value between 0 and 1), indicating: whether the input image is positive, whether the input image is positive due to malignant calcification, whether the image is positive due to a soft lesion, and whether the image is positive or benign. During the training, all 4 outputs are tuned, for example, using a binary cross-entropy loss. At inference time, the first prediction (i.e., whether the input image is positive) may be used to determine the image-level score, while the other predictions are ignored.

At 316, the whole image classifier component is provided. The whole image classifier component is designed for fast inference and/or high specificity of a binary classification task in large grayscale medical images. The whole image classifier component may be implemented with a number of trainable parameters less than about 100000, or less than about 150000, or less than about 250000, which is much lower than other classifiers, such for visual light based images, which may be used for transfer learning to train image classifiers. Multiple layers of the whole image classifier are compacted, to reduce the number of layers and/or reduce processing resource requirements and/or processing time to obtain the classification outcome. Since the images are grayscale, with binary findings (or a small subset of findings, such as small subset of findings likely to be cancer) on a substantially homogenous background (e.g., tissue, such as breast, lung, liver, brain), the layers may be compacted to focus on the specific problem at hand, reducing the number of training parameters and/or reducing the number and/or size of the layers, in comparison to other standard classifiers.

At 318, an ML model ensemble is provided. The ML model ensemble may include one or more of (i) one or more two-stage detector components (e.g., trained using different initialization values) that generate dot product(s) in response to an input of the target image, (ii) one or more whole image classifier components (e.g., trained using different initialization values) that generate classification score(s) in response to the input of the target image, and code that computes a medical image level score by aggregating the dot products and the whole image classifier score(s) into a single value, as described herein.

Referring now back to FIG. 4, inference by a two-stage detector component is described. The two-stage detector component may be part of an ensemble that includes one or more two-stage detector components, and/or one or more whole image classifiers, for example, as described with reference to FIG. 5.

At 402, a medical image is fed into the trained detector component of the two-stage detector, optionally of an ensemble.

The detector component is trained on the first training dataset of medical images annotated with ground truth boxes depicting a visual finding therein, as described herein.

At 404, multiple boxes are obtained as outcomes of the detector component. The boxes may be overlays over the medical image, represented as coordinates within the medical image, and/or other representation may be used. Each respective box is associated with a respective box score indicative of likelihood of the visual finding being depicted therein, for example, a probability score from 0-1.

The detector component generates at least 50, 75, 100, 150, 200, 250, 500, 1000, or greater or intermediate number of boxes. Boxes having highest box scores may be selected, for example, the top 150 of 1000 boxes may be selected.

Optionally, boxes are generated per classification outcome, for example, 75 boxes for soft lesions, and 75 boxes for calcifications, for a total of 150 boxes indicating positive for the visual finding.

Boxes may be of varying size and/or at various locations throughout the image. Boxes may overlap with the visual finding, for example, by at least about 50%, or 60%, or 70%, or 80%, or 90%, or other values.

As described herein, Inventors discovered that a large number of boxes increase the accuracy of detecting the visual finding by the two-stage detector. The dot product computed based on the large number of boxes increases the accuracy of detecting the visual finding.

The detector may be configured to generate a relaxed non-maximum suppression setting for Intersection over Union threshold, for example, 0.7, 0.8, 0.9, 0.95, 0.96, 0.97, 0.98, and 0.99.

Boxes may overlap with one another. The overlap provides redundancy, which may act as a form of test time augmentation for the patch classifier.

At 406, the box scores may be duplicated, or tripled, or quadrupled, or increased by another factor. For example, the box scores are scored as a vector, which is then copied and the copy appended to the original vector.

At 408, each respective box is converted into a respective patch. The patch may be obtained by extracting a portion of the image defined by the box, and resizing the extracted portion to a common patch size. Different sized extracted portions corresponding to different sized boxes are converted to the common patch size, for example, to 299×299 or other dimensions.

At 410, an image processing operation may be performed on each of the boxes to generate a double, or tripling, or quadrupling, or other multiple, of the boxes. The image processing operation may be, for example, a vertical flip, a horizontal flip, and/or a mirror reflection along a selected axis.

The multiple used correspond to the multiple used for the scoring in 406, such that the number of box scores matches the number of overall boxes (including the boxes generated as outcomes of the detector and the boxes generated from the image processing operation).

The multiple (e.g., double) of the boxes are converted to the multiple (e.g., double) of the patches, The multiple (e.g., double) of the patches are fed into the patch classifier. It is noted that when the multiple (e.g. double) of the patches is not implemented, the patches are fed into the classifier.

The patch classifier may be implemented as a convolutional neural network (CNN) trained on the second training dataset that includes patches extracted from the ground truth box labels of the first training dataset. The image processing operation may be applied during the training, to include patches created from the image processing operation in the second training dataset.

At 412, in response to the input of the patches into the patch classifier, patch score are obtained as an outcome of the patch classifier. Each respective patch is associated with a respective patch score indicative of likelihood of the visual finding being depicted therein.

When the multiple (e.g., double) of the patches are fed into the patch classifier, multiple score are obtained.

At 414, a dot product of the box scores and the patch scores is computed.

When the multiple (e.g., double) of the box scores and the multiple (e.g., double) of the patch scores are computed, the dot product is between the duplicated multiple box scores and the double of the multiple patch scores.

Each respective patch score obtained from the patch classifier for a respective patch corresponds to a respective box score obtained from the detector component from the respective box corresponding to the respective patch. The dot product is computed by considering the correspondence between patch scores and box scores. For example, a first vector of patch scores is created, and a second vector of box scores is created, where each position in the first and second vectors indicates a correspondence. The dot product is computed between the first and second vectors.

The dot product is provided as an image-level indication of likelihood of the visual finding being depicted in the medical image.

Referring now back to FIG. 5, a flow 500 that includes features 502-520, depicts exemplary ensemble inference for a single image. In the case of a series of multiple images, for example, a set of 4 standard views of left and right side mammographic images, features 502-520 may be iterated to obtain a stud-level score based on the multiple images, for example, as described with reference to FIG. 6.

It is noted that the ensemble described herein is exemplary and not necessarily limiting. Other number of components may be used, for example, by searching candidates for a best combination that provides a highest area under curve (AUC) (e.g., as described in the Examples section below).

At 502, the medical image is accessed, for example, the medical image is obtained from a PACS, and/or other storage device.

At 504, the medical image and/or data associated with the medical image (e.g., metadata, such as DICOM metadata) may be analyzed to determine whether to further process or exclude the medical image. For example, a filter, such as a set of rules, may be used to determine which medical images to exclude. The exclusion may be for types of medical images which were excluded from the training datasets. It is noted that specialized classifiers and/or detectors may be trained on excluded images, to create specialized classifiers and/or detectors for special cases. Exemplary criteria for excluding images include one or more of: type of imaging sensor (e.g., manufacturer, model), males, age under 40, implants, image series that is missing standard images or includes too many images (e.g., mammography images that do not include standard 4 views), indication of previous surgery, biopsy, or injury.

At 506, a series matcher code may feed the image into each component of the ensemble. Images may be cropped to mostly or only include a target region of interest which is analyzed by the two-stage detector and/or whole image classifier, for example, the breast for mammographic images, lungs and/or liver for x-ray and/or CT images.

At 508, the image is inputted into each component of the ensemble, for example, Inferencer 1 which may be a first whole image classifier component (e.g. CNN) 510, Inferencer 2 which may be a second whole image classifier component (e.g., trained using different initialization weights) 512, Inferencer 3 which may be a first two-stage detector 514, and Inferencer 4 which may be a second two-stage detector 516 (e.g., trained using different initialization weights).

It is noted that two implementations of the two-stage detector and/or two implementations of the whole image classifier component are exemplary and not necessarily limiting, and other numbers of implantations may be used.

At 518, the whole image classifier scores, also referred to as classification scores (denoted score 1 and score 2) generated by whole image classifier components 510 and 512, and the dot products (denoted score 3 and score 4) generated by two-stage detectors 514 and 516 are aggregated into a single value of a medical image level score (also referred to as final study score), for example, by computing an average thereof, optionally a weighted average.

At 520, a threshold is applied to the medical image level score to obtain the final classification outcome for the image. For example, when the medical image level score is above the threshold, the classification outcome may be suspicious for the visual finding. When the medical image level score is below the threshold, the classification outcome may be not suspicious for the visual finding Referring now back to FIG. 6, the features described with reference to FIG. 6 may be performed for each component, i.e., each two-stage detector and/or each whole image classifier, which may be components of the ensemble.

At 602, a series of multiple target images may be received. The series of multiple target images may be for a single subject for a single study session, for example, each series of medical images may include a set of four mammographic images including two images for a left side and two images for a right side obtained at standard views as part of a standard breast screening example. For example, left craniocaudal (LCC), left mediolateral oblique (LMLO), right craniocaudal (RCC), and right mediolateral oblique (RMLO).

At 604, the series of images are inputted into each component, i.e., each two-stage detector and/or each whole image classifier, which may be components of the ensemble.

At 606, input factory code may control the inputting of each of the images of the sequence, i.e., each one of LCC, LMLO, RCC, and RMLO is fed into each component. The feeding may be performed sequentially, or in parallel where a parallel processing architecture enables parallel processing of different images.

At 608, each of the images of the sequence (e.g., LCC, LMLO, RCC, and RMLO) is fed into a respective component, generically denoted "IM". The respective component computes a respective image-level score (e.g., a respective mammographic image score) for each respective image.

At 610, a left side aggregated score (e.g., a mean mammographic image score for the left side) is computed for the images of the left side. For example, the mean of the LMLO and LCC images.

At 612, a right side aggregated score (e.g., a mean mammographic image score for the right side) is computed for the images of the right side. For example, the mean of the RMLO and RCC images.

At 614, a series-level aggregated score (e.g., a maximum mammographic image score) is computed from the left side aggregated score and the right side aggregated score. For example, the series-level aggregated score is obtained as the maximum of the left side aggregated score and the right side aggregated score.

At 616, features 606-614 are iterated, where at each iteration one or more augmentations are performed, for example, augmentations are performed for each mammographic image of the series of 4 mammographic images. Each augmentation iteration may be assigned an augmentation ID, for example, aug 1, aug 2, aug 3, and the like. The number of augmentation iterations may be, for example, 2-10, or 3-7, or 5, or other numbers.

Exemplary augmentations include: add random noise to the top and/or bottom coordinates up to a threshold of box height (e.g., 5%), add random noise to the left and/or right coordinates up to a threshold of box width (e.g., 5%), crop patch from image and resize to the common patch size, randomly flips (vertical and/or horizontal), and/or randomly rotations by an angle (e.g., 0, 90, 180, 270, or other values).

Exemplary augmentations may be selected from a pool of multiple randomly sampled transformations, by selecting the set of transformations that optimized the area under curve (AUC) over a tuning set.

A respective series-level augmentation scores (e.g., maximum mammographic image score) is computed by each of the augmentation iterations.

At 618, the multiple series-level augmentation scores (e.g., maximum mammographic image score) computed for the plurality of augmentation iterations (e.g., as in 616) are aggregated into a series-level score (also referred to herein as "study score", or referred to as a respective classification score, e.g., respective mammographic image score). The aggregation may be performed by computing the mean of the multiple series-level augmentation scores is computed.

For the case of mammographic images, the study score may be computed by aggregating scores for the 4 image views, using the following exemplary mathematical equations:

Study_score=0.5*max(LCC$_{score}$+LMLO$_{score}$, RCC$_{score}$+RMLO$_{score}$)

Various embodiments and aspects of the present invention as delineated herein above and as claimed in the claims section below find experimental and/or calculated support in the following examples.

EXAMPLES

Reference is now made to the following examples, which together with the above descriptions illustrate some embodiments of the present invention in a non-limiting fashion.

Inventors conducted experiments based on at least some implementations described herein, to evaluate accuracy of a ML model in finding cancer in mammographic images.

Data

Reference is now made to FIG. 7, which is a table 702 summarizing training data of mammographic studies, in accordance with some embodiments of the present invention. Data was collected from 3 sources. The USA set came from Intermountain Health Care (IMH), a chain of hospitals in Utah. The Israel set came from Clalit Health Care, the biggest provider in Israel. The UK set came from Optimam. The studies were all IRB, D-ID, and anonymized. The data was split by the patient id hash into training (70%), tuning (15%) and test (15%) partitions, for example, all studies of the same patient reside in the same partition.

Studies with the following conditions were removed: Not Hologic (12%), Male (0.3%), Age under 40 (1.8%), Implants (4.3%), without 4 views (23.8%), Indication of previous surgery, and biopsy or injury (7.7%).

Reference is now made to FIG. 8, which is a table 802 summarizing categories into which the remaining studies (after removal of studies with conditions) in all partitions were divided into, in accordance with some embodiments of the present invention. Studies that did not fall into one of the categories were excluded. Two years was used as the time period for normal negative follow-up, since this is the common interval between screening exams in the US. BIRADS 5 studies are "Highly Suggestive of Malignancy" according to the American College of Radiology. BIRADS 3 are "probably benign" by the ACR. In order to get additional information about the malignancy (needed for training and evaluation) the studies in the Positive, Validated Positives, and Benign categories were sent to radiologists trained to read mammograms. The radiologists were asked to annotate a bounding box around the suspicious lesion as described in the biopsy data (when available), and specify the type of lesion (either calcification or soft-lesion), and density of the breast (4 standard levels). Hence, for those cases it was recorded for each breast whether it was negative, or had a positive or benign finding, and for the positive breasts it was known whether the malignancy was calcification or a soft-lesion.

Tuning Set Preparation

Cases collected from the tuning partition make up the tuning set. Only Validated Negatives and Validated Positives cases were used, at most one case per patient. The tuning set had 740 cases, 370 positives and 370 negatives, from the Optimam and IMH sources. Clalit data was not used for tuning since the evaluation process included also Ultrasound images that were not available.

Model Architecture

An ensemble of four ML model components (A, B, C, D) was used, where each ML model produces a study-level score. Components A and B are classifier-based, and use whole-image labels. Components C and D are detector-based, and use bounding-box annotations over the positive regions as labels. At inference time, a weighted average of those scores produces the final study score. If this final score is above the operation threshold, the study is considered positive.

The input to each model components was 4 images, corresponding to the four standard screening views (right breast: RCC, RMLO; left breast: LCC, LMLO). The images were cropped beforehand so that only the breast is shown.

Each ML model component was applied to each (cropped) breast image separately and independently, resulting in 4 distinct image-level scores per component. These scores were combined to produce the study-level score of the component according to the following formula (Equation (1)):

study_score=0:5*max(LCCscore+LMLOscore, RCCscore+RMLOscore)

For the classifier-based components test-time augmentation (TTA) was performed during inference. The same ML model component was applied 5 times, each time with a differently-augmented version of the 4 input images. The 5 resulting study-level scores were collected, and the average was used as the final study score of that ML model component. The augmentations used in the TTA were picked from a pool of 16 randomly-sampled transformations, by choosing the set of transformations that optimized the AUC over the tuning set.

For the final ensemble a pool of 18 candidate ML model components was collected. Inventors exhaustively searched the candidates for the best combination of 3, 4, and 5 components (subject to a computational constraint that only a single application of the detector is allowed). For each combination of models, a logistic regression model with L1 regularization (C=10) was fitted to weight the individual model scores, and the AUC of the resulting weighted-average was measured. This fit was done in a 5-fold cross-validation scheme over the tuning set and the mean AUC was used to score each combination. Once the winning combination was chosen the same logistic regression model was fitted over the entire tuning set and the weights were used as the ensemble weights.

Classifier Components

Each classifier-based ML component included a single neural network that is applied on each of the 4 images, and combines the resulting image-level scores based on Equation (1). The classifier model components (A and B) apply the same training procedure described herein and below, with the difference due to the random weight initialization of the network. The network's architecture was a custom-made CNN with 11-convolutional layers, designed to process large images. The CNN accepts a single 1840×1840 image as input and outputs 4 predictions (numbers between 0 and 1) indicating: whether the image is positive, whether the image is positive due to a malignant calcification, whether the image is positive due to a soft lesion, and whether the image is positive or benign.

During training, all 4 outputs were tuned using a binary cross-entropy loss. At inference time, only the first prediction was used to determine the image-level score, while the rest were discarded. Inventors discovered that the multi-task training framework improves the performance of the relevant task (the first output), and speeds up convergence. The Adam optimizer with a batch size of 12, and a learning rate of 1e-5, was used. Training was done on a NVIDIA GPU.

For augmentation, a random rotation of up to 10 degrees was applied to either side. The image was resized to a size of $(1+c_y)H$ by $(1+c_y)W$, where $c_y$, $c_y$ uniformly sampled between 0 and 0.1, and H=W=1840. A random region of size H×W=1840×1840 was cropped from the resized image.

To deal with the imbalance in the data, two different samplers were used to fill the batch content. Sampler 1 ensured equal representation for each source/label pair (the labels being "positive", "negative", "benign"). Sampler 2 ensured equal representation of each breast density (but no control over the data source and label). Sampler 1 was used to fill 80% of the batch positions and the rest were filled with sampler 2.

Training Data

Reference is now made to FIG. 9, which is a table 902 summarizing training data used in the experiment, in accordance with some embodiments of the present invention. The training set for the classifier includes images collected from the training partition, each marked as either "positive", "negative", or "benign". Cases in the categories Validated Negatives and Negatives contributed 4 "negative" images (corresponding to the 4 standard screening views). Cases from the categories Positives and Validated Positives contributed "positive" images from the malignant breasts only. Cases from the Benign category contributed both "benign" images (from the side with benign lesion) and "negative" images (from the other side). Overall, the curated training set had 23,468 positive images and 62,412 negative images.

Detector Components

Components C and D in the final ensemble included two stages. The first stage, which is shared between the components, was a standard detector, which was used to generate proposals for malignant regions in the 4 input images. In the second stage, each component applied a (separately-trained) patch-classifier on the proposals, and combined the resulting confidence scores with the ones given by the detector to produce an image-level score. Then, each component used Equation (1) to produce a study-level score.

Given the input image, the detector outputted a list of 150 boxes, and associated malignancy scores (between 0 and 1). The image-patches in those boxes were cropped and resized all to the same size (299×299). The patches were further augmented with their vertical flip to obtain 300 patches. The patches were then fed to a CNN (Inception V3), which scored them for malignancy. The dot product between these 300 scores and their corresponding detector-given box scores was computed (the same box score for the patch and its vertical flip were used), to obtain the image score.

First-Stage Detector

The detector model was implemented as RetinaNet50 (e.g., as described with reference to Tsung-Yi Lin, Priya Goyal, Ross B. Girshick, Kaiming He, and P. Dollár. *Focal loss for dense object detection*. 2017 IEEE International Conference on Computer Vision (ICCV), pages 2999-3007, 2017, incorporated herein by reference in its entirety), which is widely used for object detection. The Tensorflow Object Detection API module (part of TensorFlow Official Models 1.8.1) was used, without additional changes to the code. The network architecture used a Feature Pyramid Network (FPN) (e.g., as described with reference to Tsung-Yi Lin, P. Dollár, Ross B. Girshick, Kaiming He, B. Hariharan, and S. Belongie. *Feature pyramid networks for object detection.* 2017 IEEE Conference on Computer Vision and Pattern Recognition (CVPR), pages 936-944, 2017, incorporated herein by reference in its entirety), backbone on top of a feedforward ResNet50 architecture (e.g., as described with reference to Kaiming He, X. Zhang, Shaoqing Ren, and Jian Sun. *Deep residual learning for image recognition.* 2016 IEEE Conference on Computer Vision and Pattern Recognition (CVPR), pages 770-778, 2016, incorporated herein by reference in its entirety) to generate a rich, multi-scale convolutional feature pyramid. To this backbone the model attaches two subnetworks, one for classifying anchor boxes, and one for regressing from anchor boxes to ground-truth object boxes. The model was trained using the manually labeled ROIs, and their class label (soft lesion, calcification).

The input breast images were resized to 2880×1440 and converted to 8-bit RGB (by replicating the single channel thrice), as required by the code. The detector was configured to produce the top-scoring 75 boxes of each class (soft lesions and calcifications) after a 'relaxed' non-maximum suppression setting of 0.96 Intersection over Union (IOU) threshold. Many of these output boxes overlap with others, and this redundancy was used as a form of test-time augmentation for the second stage.

Random cropping and horizontal flip augmentations were performed to aid generalization. To speed up convergence, a warm-up phase with a reduced resolution of 1024×832 for 77,000 iterations was added. Then a switch was made to the larger resolution of 2880×1440 for the rest of the training (which took 125 k more iterations), and the checkpoint that maximized the mAP@50 IOU metric (i.e. the mean average precision, when a detection requires 50% intersection over union with ground truth) was selected. The training was performed using a single NVIDIA Quadro GV100.

Detector Training Data

Positive (biopsy-proven) studies from the training partition with box annotations over the malignant findings were extracted. These annotations were classed as soft tissue lesions or suspicious calcifications (or both, in rare cases). Negative studies were not explicitly collected, as plenty of negative supervision came from unannotated regions of the image (i.e., 'background'), or from the other breast in the study that usually did not have a finding in it.

The training set had 3,590 studies from two data sources (1549 from Clalit, 2042 from Optimam). It is noted that no studies from the third data source, IMH, were used for training. In total, there were 6,818 boxes in the training set (rarely more than one box per image, but often two views in a study would each have a box).

Second-Stage Patch Classifier

The patch classifiers in model components C and D both use the Inception V3 architecture (e.g., as described with reference to Christian Szegedy, V. Vanhoucke, S. Ioffe, Jon Shlens, and Z. Wojna. *Rethinking the inception architecture for computer vision.* 2016 IEEE Conference on Computer Vision and Pattern Recognition (CVPR), pages 2818-2826, 2016, incorporated herein by reference in its entirety), with image input size of 299×299×1 and a single output, corresponding to the patch probability of malignancy (between 0 and 1). A binary cross-entropy was used as the loss function.

Before choosing the training set of the patch classifier, the trained detector from the first stage was run over the images of studies in the training partition. Negative patches were extracted from 1,000,000 boxes that were produced by the trained-detector on images from the Validated Negatives category (which the detector didn't train on). For positive examples, patches were extracted from the 6,818 ground-truth positive boxes used to train the detector, and additionally from 195,000 boxes that were produced by the trained-detector and had an overlap of at least 0.85 IOU with a ground-truth box.

The patches were fed to the CNN in batches of 32. During training, half of each batch included negative patches, while the other positive half was divided evenly between the ground-truth boxes and the detector-produced boxes. The following preprocessing and augmentation steps were applied to each patch:

Add random noise to the Top and Bottom coordinates, up to ±5% of box height.
Add random noise to the Left and Right coordinates, up to ±5% of box width.
Crop patch from image and resize to 299×299.
Randomly flip patch vertically or horizontally.
Randomly rotate patch by 0, 90, 180, or 270 degrees.

The ML model in component D was trained from scratch for 160,000 iterations, using the Adam optimizer, with learning rate 1e-4. The model in component C was trained from ImageNet pre-trained weights using the SGD optimizer with momentum. In phase 1, which had a high-learning rate (6e-3), the single top-scoring box from each negative image was used. In phase 2, which had a lower learning rate (3e-4), the top 10 scoring boxes were used. For both components, we the model checkpoint that maximized the AUC over a held-out tuning set was used.

Results

Figure 10:
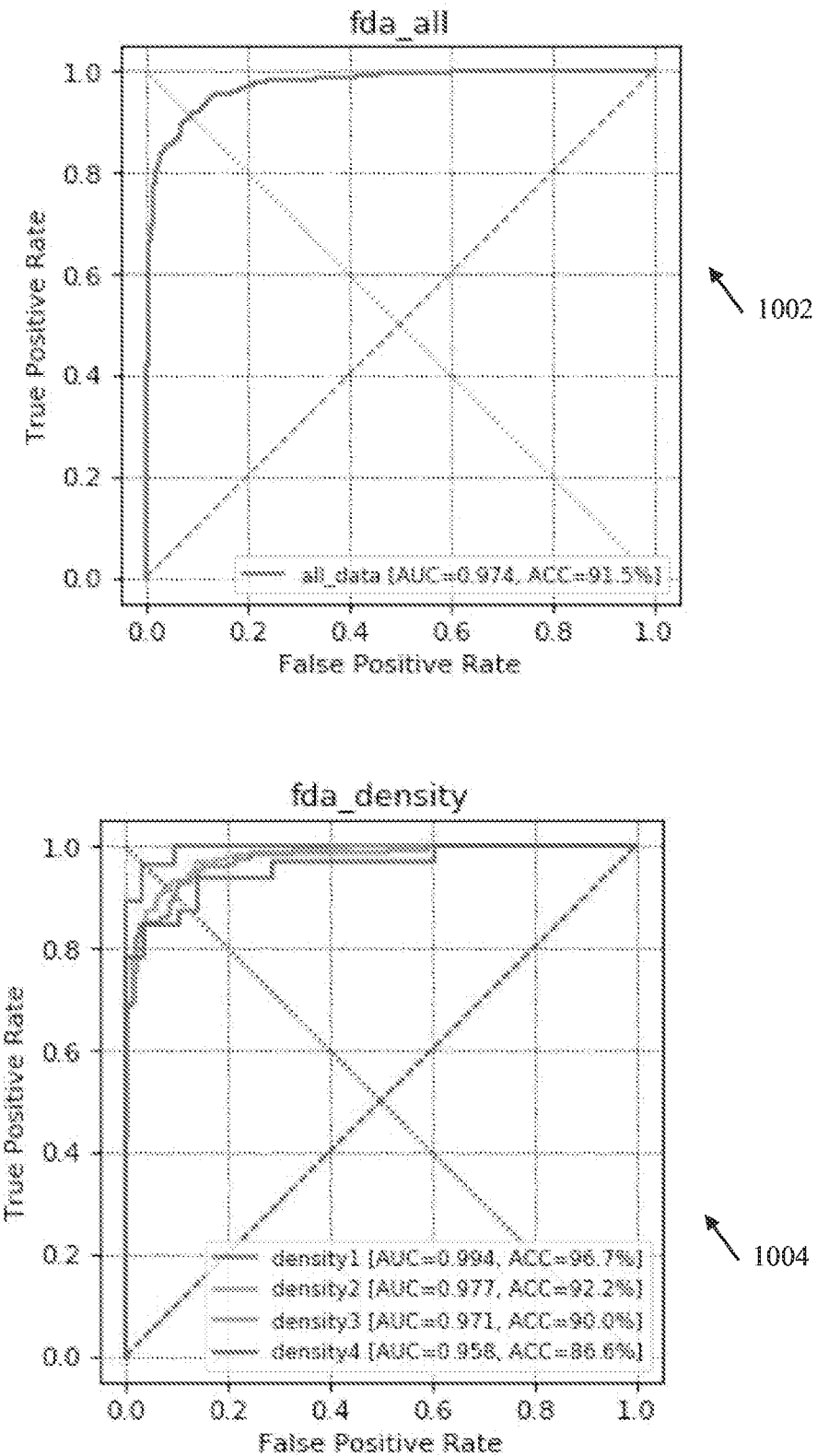
FIG. 10 includes graphs depicting receiver operating characteristic (ROC) curves, area under ROA curve (AUC) scores, and accuracy (ACC) scores, obtained as outcomes of the experiment, in accordance with some embodiments of the present invention.

Reference is now made to FIG. 10, which includes graphs 1002-1006 depicting receiver operating characteristic (ROC) curves, area under ROA curve (AUC) scores, and accuracy (ACC) scores, obtained as outcomes of the experiment, in accordance with some embodiments of the present invention. Graph 1002 depicts AUC and ACC results over the entire test set. Graph 1004 depicts AUC and ACC results broken down by density types. Graph 1006 depicts AUC and ACC results per type of malignancy.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant detectors and classifiers will be developed and the scope of the term detector and classifier is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method of identifying a visual finding in a medical image using a two-stage detector, comprising:
    feeding a medical image into a detector component implemented as a ML model trained on a first training dataset of a plurality of medical images annotated with ground truth boxes depicting a visual finding therein;
    obtaining as an outcome of the detector component, a plurality of boxes for the medical image, each respective box associated with a respective box score indicative of likelihood of the visual finding being depicted therein;
    converting each respective box into a respective patch;
    feeding each one of a plurality of patches into a patch classifier implemented as a convolutional neural network (CNN) trained on a second training dataset that includes patches extracted from the ground truth box labels of the first training dataset,
    wherein a respective patch score obtained from the patch classifier for a respective patch corresponds to a respective box score obtained from the detector component from a respective box corresponding to the respective patch;
    obtaining as an outcome of the patch classifier, a plurality of patch scores, each respective patch associated with a respective patch score indicative of likelihood of the visual finding being depicted therein;
    computing a dot product of the plurality of box scores and the plurality of patch scores; and
    providing the dot product as an image-level indication of likelihood of the visual finding being depicted in the medical image.

2. The computer implemented method of claim 1, wherein the detector component generates at least 50 boxes.

3. The computer implemented method of claim 1, wherein boxes having highest box scores are provided as the plurality of boxes.

4. The computer implemented method of claim 1, further comprising:
    duplicating the plurality of box scores;
    performing an image processing operation on each of the plurality of boxes to generate a double of the plurality of boxes, wherein converting comprises converting the double of the plurality of boxes to a double of the plurality of patches, wherein feeding comprises feeding the double of the plurality of patches, wherein a double of the plurality of patch scores is obtained as the outcome of the patch classifier;
    wherein computing the dot product comprising computing the dot product of the duplicated plurality of box scores and the double of the plurality of patch scores.

5. The computer implemented method of claim 1, wherein the detector component is trained on the first training dataset that includes for each medical image annotated with the ground truth box label, an indication of a category selected from a plurality of categories for the visual finding,
    wherein the plurality of boxes and the plurality of box scores are for the plurality of categories,
    wherein the patch classifier is trained on the second training dataset that includes patches extracted from the ground truth boxes of the first training dataset, each labelled with a single indication denoting all of the plurality of categories of the first training dataset.

6. The computer implemented method of claim 1, further comprising:
    feeding a plurality of sample medical images labelled with a ground truth negative label and excluded from the first training dataset, into the detector component, to obtain an outcome of a plurality of boxes denoting negatives;
    extracting the plurality of boxes denoting negatives as a plurality of negative patches;
    adding the plurality of negative patches labelled with an indication of negative to the second training dataset.

7. The computer implemented method of claim 1, further comprising:
    feeding a plurality of sample medical images labelled with a ground truth positive label into the detector component, to obtain an outcome of a plurality of boxes denoting positive;
    extracting the plurality of boxes denoting positive as a plurality of positive patches;
    adding the plurality of positive patches labelled with an indication of positive to the second training dataset.

8. The computer implemented method of claim 7, further comprising selecting a subset of the plurality of boxes denoting positive having an overlap over a threshold of intersection over union (IOU) with the ground truth box label.

9. The computer implemented method of claim 5, wherein an equal number of boxes and corresponding box scores are generated for each category of the plurality of categories.

10. The computer implemented method of claim 5, wherein the first training dataset includes mammographic images depicting a plurality of views of left and right breasts, and the category is selected from soft lesion and calcification.

11. The computer implemented method of claim 10, wherein the dot product indicates likelihood of breast cancer, and further comprising treating a subject for breast cancer using a treatment effective for breast cancer, selected from a group consisting of: biopsy, radiation therapy, chemotherapy, immunotherapy, surgical excision, and combinations of the aforementioned.

12. The computer implemented method of claim 1, further comprising
    feeding the medical image into a whole image classifier component trained on a whole image classifier training dataset of a plurality of sample medical images of a plurality of subjects each labelled with an indication of positive or negative,
    obtaining a whole image classifier score as an outcome of the whole image classifier component; and
    obtaining a medical image level score by aggregating the whole image classifier score and the dot product into a single value.

13. The computer implemented method of claim 12, wherein the whole image classifier component is designed for fast inference and high specificity of a binary classification task in large grayscale medical images, the whole image classifier component implemented with a number of trainable parameters less than about 150000, wherein a plurality of layers are compacted.

14. The computer implemented method of claim 12, further comprising:
    feeding the medical image into each of a plurality of detector components trained using different initialization values to obtain a plurality of dot products;

feeding the medical image into each of a plurality of whole image classifier components trained using different initialization values to obtain a plurality of classification scores; and obtaining the medical image level score by aggregating the plurality of dot products and the plurality of whole image classifier scores into the single value.

15. The computer implemented method of claim 14, wherein each medical image comprises a set of four mammographic images including two images for a left side and two images for a right side, wherein a respective classification score is computed by computing a respective mammographic image score for each of the four mammographic images, computing a maximum mammographic image score of a mean mammographic image score for the left side and a mean mammographic image score for the right side, wherein the maximum mammographic image score is provided as the respective classification score.

16. The computer implemented method of claim 15, further comprising computing a plurality of augmentation sets for the set of four mammographic images, wherein a respective maximum mammographic image score is computed for each of the plurality of augmentation sets, computing a mean of a plurality of the maximum mammographic images scores, and providing the mean as respective classification.

17. The computer implemented method of claim 12, wherein the indication of positive includes: positive due to a plurality of sub-categories, benign, and one of the plurality of sub-categories defined as positive;

wherein the whole image classifier component is trained using the training dataset for outputting a value for each of a plurality of categories consisting of: positive due to a plurality of sub-categories, benign, one of the plurality of sub-categories defined as positive; and wherein obtaining the whole image classifier score as the outcome of the whole image classifier component comprises obtaining a target value for the category of positive due to the plurality of sub-categories, and discarding other target values of other categories.

18. The computer implemented method of claim 12, wherein each image is a whole high resolution mammographic image selected from a group consisting of left craniocaudal (LCC), left mediolateral oblique (LMLO), right craniocaudal (RCC), and right mediolateral oblique (RMLO) having resolution at least greater than 1840×1840, wherein the plurality of sub-categories are selected from a group consisting of: malignant calcification, and soft lesion.

19. A computer implemented method of creating a two-stage detector ML model for identifying a visual finding in a target medical image, comprising:

accessing a first training dataset including a plurality of medical images annotated with ground truth boxes depicting the visual finding therein;

training a detector component using the first training dataset for generating, in response to an input of the target medical image, an outcome of a plurality of boxes and a plurality of box scores each indicative of likelihood of the visual finding being depicted in a respective box;

accessing a second training dataset that includes patches extracted from the ground truth box labels of the first training dataset, the patches labelled with the ground truth corresponding to the box labels;

training a patch classifier component using the second training dataset for generating, in response to an input of a plurality of patches obtained from the plurality of boxes generated by the detecting component, a plurality of patch score, each respective patch associated with a respective patch score indicative of likelihood of the visual finding being depicted therein; and providing the two-stage detector ML model, comprising of: the detector component, the patch classifier, and code for computing a dot product of the plurality of box scores and the plurality of patch scores, wherein the two-stage detector ML model generates the dot product as an image-level indication of likelihood of the visual finding being depicted in an input target medical image.

20. The computer implemented method of claim 19, further comprising providing an ensemble of ML models by:

training a whole image classifier component by:

accessing a whole image classifier training dataset of a plurality of sample medical images of a plurality of subjects each labelled with an indication of positive or negative, training the whole image classifier component for generating a whole image classifier score as an outcome in response to an input of the target medical image; and providing a ML model ensemble comprising: a plurality of two-stage detector components trained using different initialization values that generate a plurality of dot products in response to an input of the target image, a plurality of whole image classifier components trained using different initialization values that generate a plurality of classification scores in response to the input of the target image, and code that computes a medical image level score by aggregating the plurality of dot products and the plurality of whole image classifier scores into a single value.

* * * * *